(12) United States Patent
Nachtkamp et al.

(10) Patent No.: US 8,722,092 B2
(45) Date of Patent: May 13, 2014

(54) NANOPARTICLES MADE OF AMORPHOUS CELLULOSE

(75) Inventors: Klaus Nachtkamp, Walsrode (DE); Jürgen Engelhardt, Bad Fallingbostel (DE); Christa Krüger, Schneverdingen (DE); Steffen Fischer, Freital (DE); Manfred Pinnow, Teltow (DE); Kay Hettrich, Caputh (DE)

(73) Assignee: Dow Global Technologies LLC, Midland, MI (US)

( * ) Notice: Subject to any disclaimer, the term of this patent is extended or adjusted under 35 U.S.C. 154(b) by 477 days.

(21) Appl. No.: 12/672,824

(22) PCT Filed: Aug. 8, 2008

(86) PCT No.: PCT/EP2008/006546
§ 371 (c)(1),
(2), (4) Date: Feb. 9, 2010

(87) PCT Pub. No.: WO2009/021687
PCT Pub. Date: Feb. 19, 2009

(65) Prior Publication Data
US 2011/0293732 A1    Dec. 1, 2011

(30) Foreign Application Priority Data
Aug. 10, 2007 (EP) .................................... 07015804

(51) Int. Cl.
*A61K 9/14* (2006.01)
*A61K 31/717* (2006.01)
*A61K 47/38* (2006.01)

(52) U.S. Cl.
USPC ............... 424/489; 127/37; 514/781; 524/13; 524/35; 977/773

(58) Field of Classification Search
None
See application file for complete search history.

(56) References Cited

U.S. PATENT DOCUMENTS

| 429,534 | A | | 2/1890 | Khotinsky |
| 3,397,198 | A | | 8/1968 | Greidinger et al. |
| 4,374,702 | A | | 2/1983 | Turbak et al. |
| 5,417,984 | A | | 5/1995 | Banker et al. |
| 5,674,507 | A | * | 10/1997 | Banker et al. ................. 424/401 |
| 6,174,358 | B1 | * | 1/2001 | Oberkofler et al. ......... 106/200.1 |
| 6,379,594 | B1 | * | 4/2002 | Dopfner et al. ................. 264/28 |
| 6,534,071 | B1 | | 3/2003 | Tournilhac et al. |
| 7,357,339 | B2 | | 4/2008 | Kondo et al. |
| 2005/0239744 | A1 | | 10/2005 | Ioelovich et al. |
| 2005/0272836 | A1 | * | 12/2005 | Yaginuma et al. .............. 524/27 |

FOREIGN PATENT DOCUMENTS

| CN | 1470552 | 1/2004 |
| JP | 2000-26229 | 1/2000 |
| WO | 2006034837 A2 | 4/2006 |

OTHER PUBLICATIONS

P Kleinebudde, M Jumaa, FE Saleh. "Influence of Degree of Polymerization on Behavior of Cellulose During Homogenization and Extrusion/Spheronization." AAPS Pharmsci, vol. 2(2), 2000, article 21, pp. 1-10.*
H Zhao, JH Kwak, Y Wang, JA Franz, JM White, JE Holladay. "Interactions between cellulose and N-methylmorpholine-N-oxide." Carbohydrate Polymers, vol. 67, 2007, pp. 97-103, available online Jun. 9, 2006.*
Voigt; "Anorganische Salzhydratschmelzen—ein unkonventionelles Lose- und Reaktionsmedium fur Cellulose"; Translation Needed, Inorganic Salt Hydrate Metals—an unconventional dissolution and reaction medium for cellulose, Mar. 19, 2003, 202 full pages.
Hermans et al.; "On the Recrystallization of Amorphous Cellulose"; The Recrystallization of Amorphous Cellulose; 1946; pp. 2547-2552.
Ioelovich et al.; "Microcrystalline Cellulose: Nano-Structure Formation"; Cellulose Chemistry and Technology; 2006; pp. 313-317; vol. 40; Issue 5.
Kim et al.; "Structural Studies of Electrospun Cellulose Nanofibers"; Polymer; 2006; pp. 5097-5107; vol. 47.
Miriam De Souza Lima et al.; "Rodlike Cellulose Microcrystals: Structure, Properties, and Applications"; Macromolecules Rapid Communication; 2004; pp. 771-787; vol. 25; Wiley-VCH Verlag GmbH & Co. KGaA; Weinheim.
Ono et al.; "New Aqueous Dispersion of Cellulose Sub-micron Particles: Preparation and Properties of Transparent Cellulose HydroGel(TCG)"; Transactions of the Materials Research Society of Japan; 2001; pp. 569-572; vol. 26; Issue 2.
Zhang et al.; "Facile Synthesis of Spherical Cellulose Nanoparticles"; Carbohydrate Polymers; 2007; pp. 607-611; vol. 69; Elsevier Ltd.

* cited by examiner

*Primary Examiner* — Frederick Krass
*Assistant Examiner* — Isaac Shomer

(57) ABSTRACT

The present invention provides novel nanoscale cellulose particles and also a process for their production. The cellulose-based particles obtained have volume-averaged particle sizes of less than 300 nm. These nanoparticles are produced from amorphous cellulose or by amorphization of cellulose, optional subsequent hydrolysis and by input of energy into a water-containing medium after or during dispersion.

11 Claims, 2 Drawing Sheets

NANOPARTICLES MADE OF AMORPHOUS CELLULOSE

CROSS REFERENCE TO RELATED APPLICATIONS

Figure 1:
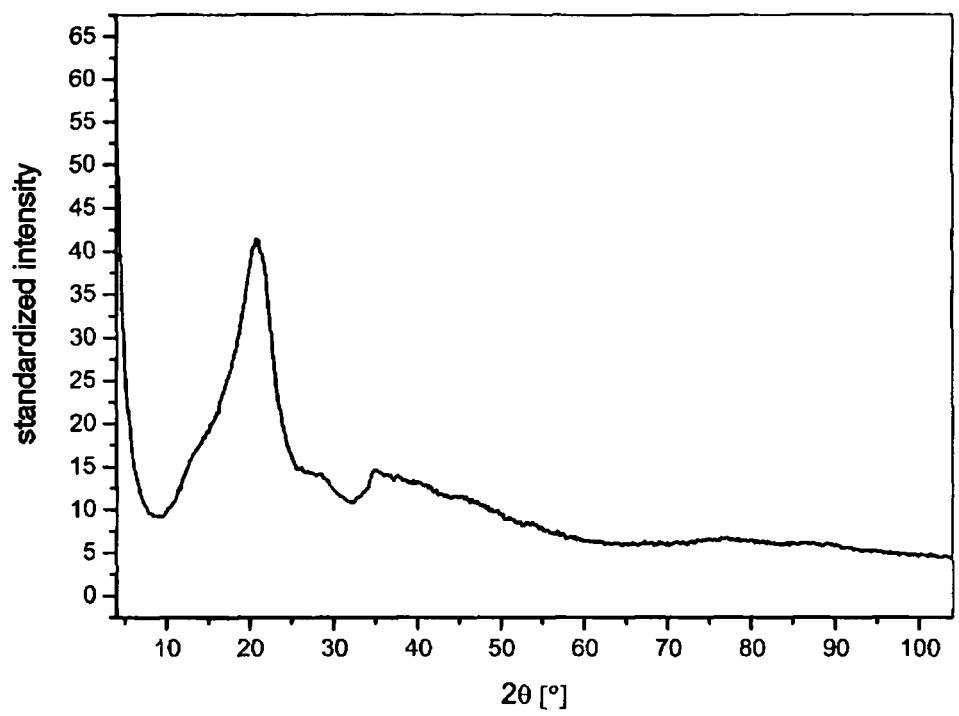

This application is a 35 USC §371 national phase filing of PCT/EP08/06546 filed Aug. 8, 2008, which claims the benefit of European Application No. 07015804.3, filed Aug. 10, 2007.

The present invention relates to novel nanoscale cellulose particles of amorphous cellulose and also to a process for their production and to the use.

Alongside information technology and biotechnology, nanotechnology is regarded as the major technological development of our times. In general, nanotechnology is concerned with the construction, properties and effect/activity of structures measuring several hundred nanometers (nm) or less. Applications are arising in almost all areas of everyday life, for example energy technology, environmental technology, information technology and the pharmaceutical and medical sector.

Cellulose is the most commonly occurring biopolymer on Earth and therefore the globally most significant renewable raw material. As the main constituent of the scaffolding substance in plants, a cellulose has outstanding molecular properties. Even in its natural state it contains ordered regions (crystallites) having the typical dimensions of nanoparticles (3-10 nm wide and up to 100 nm long). These regions, however, are connected to each other via non-crystalline macromolecules and also via secondary valency bonds (hydrogen bonds).

Various approaches have hitherto been pursued to produce cellulose-based nanoparticles which are very substantially free of superstructures. Their common idea is for individual particles of cellulose to be separated from one another and stabilized to arrive at primary particles which are not bonded together by hard irreversible agglomeration.

This typically involves mechanical and/or chemical operations (De Souza Lima, Borsali, Macromol. Rapid Commun. 25 (2004) 771, Ono, Shimaya, Hongo, Yamane, Transactions of the Materials Research Society of Japan 26 (2001) 569, Ioelovich, Leykin, Cellulose Chem. Technol. 40 (2006) 313, Zhang, Elder, Pu, Ragauskas, Carbohydr. Polym. 69 (2007) 607, US-A 2005 0239744, WO 2006/034837 A2, EP 1582551 A1, DE 3047351 C2).

CN 1470552 discloses the production of cellulose particles on the order of 50 to 200 nm in size wherein cellulose is initially dissolved in a suitable solvent and subsequently dispersed by intensive stirring into a sedimentation solution. Stabilizing the particles which form in the process requires the addition of external emulsifiers such as fatty acid salts or alkylbenzenesulphonates. This process provides only extremely dilute dispersions having a cellulose content of below 0.5% by weight.

However, the results of these methods are unsatisfactory with regard to fineness and convenience. This is because many of the processes described in the literature lead to fibrillar particles which are nanoscale in cross section only and have fibre lengths of distinctly above 300 nm. Hitherto nanoscale particles could only be obtained via very costly and inconvenient processes which lead to particles having a high degree of crystallinity. Furthermore, the addition of external stabilizers, which are not covalently bonded to the particles, is undesirable, since these stabilizers can be washed off or disrupt many applications, for example in the field of pharmaceutical formulations.

It is an object of the present invention to provide novel cellulose-based nanoparticles which are dispersible to primary particles and are obtainable by a technically comparatively straightforward process and do not require external emulsifiers for particle formation.

We have found that this object is achieved by shearing or ultrasonic dispersion of very substantially amorphous cellulose.

The present invention accordingly provides particles of amorphous cellulose having volume-averaged particle sizes (D50 value) of less than 300 nm, preferably less than 200 nm and more preferably 100 nm, measured by dynamic laser light scattering.

The present invention likewise provides a process for producing dispersions containing particles of amorphous cellulose having volume-averaged particle sizes (D50 value) of less than 300 nm, preferably less than 200 nm and more preferably less than 100 nm, determined by dynamic laser light scattering, which process comprises
a) amorphous cellulose, preferably amorphous non-nanoscale cellulose, having a less than 20% by weight fraction of crystalline regions being provided,
b) subsequently, if appropriate, being at least partially hydrolysed, and
c) thereafter being taken up in water or a water-containing liquid medium and being simultaneously or subsequently dispersed therein by input of energy and finally, if appropriate, being diluted with water.

In a preferred embodiment of the invention, the D90 value and more preferably also the D95 value of the amorphous cellulose particles is less than 300 nm, preferably less than 200 nm and more preferably less than 100 nm, the particles preferably being present agglomerate-free, i.e. dispersed to primary particles.

The amorphous cellulose, preferably amorphous non-nanoscale cellulose, suitable for step a) in the above process according to the present invention can be obtained from all commercial pulps, for example, chemical pulp, paper-grade pulp, microcrystalline cellulose or linters cellulose.

"Non-nanoscale cellulose" refers to cellulose having a volume-average particle size (D50 value) of at least 300 nm, preferably at least 200 nm and more preferably at least 100 nm, determined by dynamic laser light scattering.

The amorphous celluloses used in the process according to the present invention typically have average degrees of polymerization ($DP_{cuoxam}$) in the range from 100 to 3000, preferably in the range from 200 to 2500 and more preferably in the range from 250 to 2000 and even more preferably in the range from 350 to 1500, determined according to the method described by D. Klemm, B. Philipp, T. Heinze, U. Heinze, W. Wagenknecht in *Comprehensive Cellulose Chemistry*, Volume 1, Appendix "Determination of the DP of cellulose in Cuam solution", page 234-235, Wiley-VCH.

The amorphous cellulose having a less than 20% by weight fraction of crystalline regions in step a) of the inventive process is provided by the starting cellulose being dissolved in a solvent and subsequently reprecipitated by addition of a non-solvent.

A preferred solution/precipitation process for eliminating crystalline regions and providing an amorphous cellulose having a less than 20% by weight fraction of crystalline regions is to dissolve the starting cellulose in a solvent, such as N-methylmorpholine N-oxide monohydrate (NMMNO), such as a salt hydrate melt, for example $ZnCl_2 \cdot 4H_2O$, $LiClO_4 \cdot 3H_2O$, $FeCl_3 \cdot 6H_2O$, or such as an ionic liquid, for example 1-butyl-3-methylimidazolium chloride; and then reprecipitating the cellulose by addition of a non-solvent. Examples of such non-solvents are alcohols, water or mixtures thereof.

Instead of the above-described solution/precipitation process for providing amorphous cellulose, amorphous cellulose can also be produced by grinding (for example in a planetary mill, ball mill) (P. H. Hermans, A. Weidinger, J. Am. Chem. Soc. 68 (1946) 2547, S. Fischer, Habilitation Thesis, TU Bergakademie Freiberg 2003).

The cellulose used in step a) of the process according to the present invention has a less than 20% by weight fraction of crystalline regions, preferably less than 15% by weight fraction of crystalline regions, and more preferably less than 10% by weight fraction of crystalline regions. Crystallinity is determined using wide angle X-ray scattering (WAXS).

The optional hydrolysis in step b) can be effected, for example, by means of a mineral acid, preferably sulphuric acid or phosphoric acid, or a salt hydrate melt, preferably zinc chloride or lithium perchlorate, preferably at temperatures of 40° C. to 100° C. A hydrolysis can serve to shorten the chain length of the cellulose compounds. The term "mineral acid" also subsumes mineral acid mixtures. The term "salt hydrate melt" also comprises melt mixtures.

Preferably, after hydrolysis, the reaction mixture is freed of salts dissolved therein. This can be effected for example by centrifugation and washing with water, i.e. by removing the crude product by centrifugation, then adding water and separating the product from the wash water by centrifugation. The residual salt content of the hydrolysis product is preferably less than 5% by weight and more preferably less than 1% by weight.

Water is preferably used as medium for dispersing the particles. The pH of the aqueous medium which is not strongly acidic is preferably in the range above 5, more preferably above 6, even more preferably in the range from 6 to 10 and yet even more preferably in the range from 6.5 to 8.

In the process according to the present invention the energy input in step c) is preferably at least 2000 kWh/t, more preferably at least 5000 kWh/t and even more preferably at least 10 000 kWh/t, with regard to the mass of the amorphous cellulose provided.

Energy can be input into step c) using in principle any apparatus and technique known to a person skilled in the art. Preferably the input of energy in step b) is effected via ultrasonicators, high-speed stirrers, dispersing devices based on the rotor-stator principle (for example Ultra-Turrax® units), jet dispersers and dispersing devices of the Microfluidizer® type.

Dispersing devices based on the rotor-stator principle, e.g. Ultra-Turrax® units (available from IKA), are dispersing devices for emulsifying, homogenizing and suspending flowable media. The effective frequency is adjustable and can be conformed to the substance or mixture of substances to be processed.

The principle of a Microfluidizer® (available from Microfluidics) can be described as follows. The material to be processed is led under high pressure through an interaction chamber. The sample flows through one or two narrow pathways and reaches linear speeds of up to 1000 m/s or even more, depending on the type of instrument. This creates enormous shearing forces. There are no moving parts in the chamber, ensuring a narrow particle and droplet distribution.

"Dispersing device of the Microfluidizer® type" refers to any dispersing device comprising the following features and functions:

one or more channels for conducting a material, for example a cellulose or cellulose derivative in an aqueous medium, to an interaction chamber, the interaction chamber comprising one or more facilities, e.g. one or more rifts or noozles, the mateial is conducted under high pressure, preferably at least 20.000 MPa, more preferably 30.000 bis 300.000 MPa, to the interaction chamber, the facilities in combination with the high pressure cause in the interaction chamber an increasement of the velocity of the introduced material, preferably to at least 200 m/s, more preferably to at least 500 m/s, and even more preferably to at least 1000 m/s, and construction means allowing a pressure drop with effect to the material stream having passed the interaction chamber.

The energy input in stage c) can in principle be effected in one or more stages, but also continuously using a variable energy input.

In a preferred embodiment of the process of the invention the input of energy in step c) is effected in at least two stages comprising the input of energy in a first stage via a dispersing device based on the rotor-stator principle followed by the input of energy in a second stage via a dispersing device of the Microfluidizer® type. It is believed that in the first stage mainly the fiber structure of the cellulosic particles is disintegrated while in the microfluidizer stage mainly comminution in the nanoscale range takes place due to reduction of the chain length of the cellulose molecules.

The dispersion obtained in step c) has a solids concentration of the cellulose of preferably 0.1% to 10% by weight, more preferably 0.5% to 3.5% by weight and most preferably 0.75% to 2.5% by weight.

The dispersing effected in step c), in particular due to the input of energy, can have the effect of reducing the degree of polymerization of the amorphous cellulose. A reduction of 5 to 50% in the degree of polymerization is possible. Therefore, the nanoscale amorphous cellulose obtained in step c) can have an average degree of polymerization in the range from 50 to 2900 and preferably in the range from 100 to 2400.

The addition of dispersants or emulsifiers to stabilize the cellulose dispersion is not necessary in the process of the present invention. In a preferred embodiment of the invention, therefore, no dispersant or emulsifier, preferably no fatty acid salt or alkylbenzenesulphonate, is added before, during or after the dispersing step c). Nevertheless, further stabilization can be achieved through addition of such agents.

The process of the present invention, in particular step c), is preferably carried out at temperatures of 10 to 100° C. and more preferably 20 to 80° C.

It follows from the above described process that the present invention also provides a dispersion containing particles of amorphous cellulose, wherein the D50 value of the particles is less than 300 nm, preferably less than 200 nm and more preferably 100 nm, determined by dynamic laser light scattering, and wherein the amorphous cellulose has a less than 20% by weight fraction of crystalline regions.

Preferably, the amorphous cellulose of the dispersion according to the present invention is from chemical pulp, paper-grade pulp, microcrystalline cellulose or linters cellulose.

As mentioned above the dispersing effected in step c) of the process of the invention, in particular due to the input of energy, can have the effect of reducing the degree of polymerization of the amorphous cellulose. A reduction of 5 to 50% in the degree of polymerization is possible. Therefore, the amorphous cellulose of the dispersion according to the present invention obtained in said step c) can have an average degree of polymerization $DP_{cuoxam}$ in the range from 50 to 2900 and preferably in the range from 100 to 2400, determined as described by D. Klemm et al. in *Comprehensive Cellulose Chemistry*, Volume 1, p. 234-235.

EXAMPLES

The celluloses used were commercially available wood pulps or linters celluloses.

The cellulose derivatives were dispersed in water using a high-speed stirrer working according to the rotor-stator principle (Ultra Turrax® T25 basic, IKA, speed of rotation 20 000 $min^{-1}$).

A Microfluidizer® of the type 110F (Microfluidics, Newton Mass. USA) having two interaction chambers connected in series (H210Z 200 μm and JR20Z 50 μm) was used for further homogenization.

The wide angle X-ray measurements were carried out on D5000 two circle diffractometer from Bruker-AXS in symmetrical transmission using monochromatic Cu-Kα radiation (Ge(111) monochromator). The curves were recorded at 30 mA and 40 kV in the 2η angle range of 4-104° (step width $\Delta 2\theta = 0.2°$). The diffractometer scattering curves were evaluated with the aid of WAXS 7 IAP software (method of Ruland-Vonk) to determine a crystallinity $X_c$.

Dynamic laser light scattering measurement was carried out using a Horiba LB 550 (USA) having a measuring range from 1 nm to 6 μm. To this end, the diffusion rates of the dispersed particles are measured via the Doppler shift in the frequency of the laser light scattered by them. The frequency shifts are captured by a detector as intensity fluctuations in the scattered light. Not only the D50 (50% of the particles are smaller than the stated dimension) but also the D90 values (90% of the particles are smaller than the stated dimension) are determined.

The average degree of polymerization $DP_{cuoxam}$ was determined according to the method described by D. Klemm, B. Philipp, T. Heinze, U. Heinze, W. Wagenknecht in *Comprehensive Cellulose Chemistry*, Volume 1, Appendix "Determination of the DP of cellulose in Cuam solution", page 234-235, Wiley-VCH.

Example 1 a) Providing Amorphous Cellulose 53 g of cellulose (average degree of polymerization $DP_{cuoxam\ (tetramminecopper(II)\ hydroxide\ solution)} = 751$, crystallinity $x_c = 48\%$) were suspended in 2800 g of 46% N-methylmorpholine N-oxide solution (NMMNO) in the presence of 0.75 of propyl gallate. 1320 g of water were evaporated off at 105° C. and 60 mbar, and the cellulose dissolved. This solution was admixed with 1.5 liters of 2-propanol added incrementally at 80° C., and the cellulose precipitated. The product was separated off, washed with 2-propanol and dried in a vacuum drying cabinet. The cellulose obtained is amorphous. The DP of this sample was $DP_{cuoxam} = 657$.

FIG. 1 shows the scattering curve of the amorphous cellulose obtained. The crystallinity $x_c$ determined therefrom is 14%.

b) Preparing a Dispersion of Nanoscale Cellulose Particles 10 g of this amorphous cellulose were hydrolysed in 490 ml of 20% by weight sulphuric acid at 80° C. and 6 h. The suspension was then introduced into 1 liter of water using an Ultra-Turrax® and washed by means of a centrifuge until pH-neutral and salt free.

For dispersion, 300 ml of a 2% by weight suspension of this cellulose in water was initially treated with an Ultra-Turrax® for 30 min and then with a Microfluidizer® at 600 bar and 1100 bar for one hour each. After the microfluidizer treatment, the solids concentration was adjusted to 1.5% by weight by addition of water.

The result obtained was a completely transparent, stable and opalescent dispersion of cellulose having a $DP_{cuoxam} = 52$.

Figure 2:
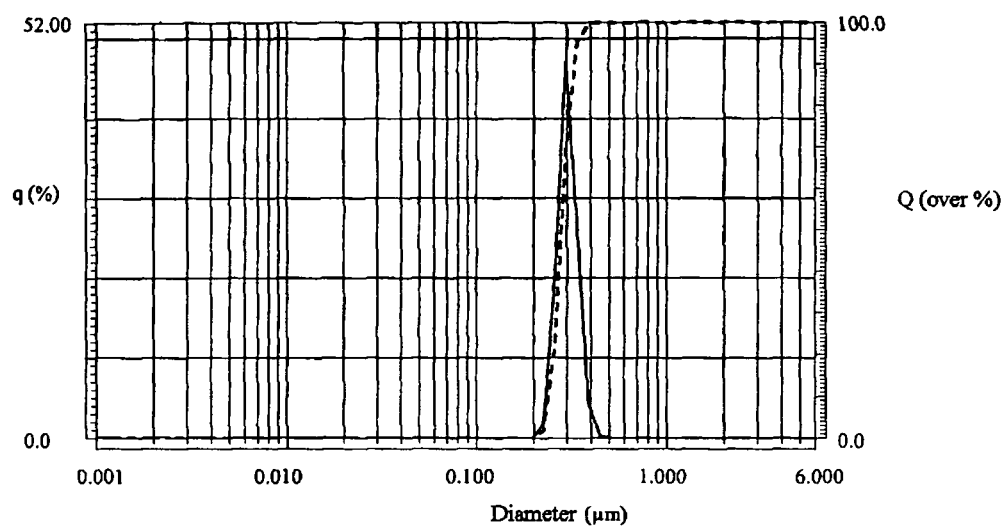

FIG. 2 shows the dynamic laser light scattering measurement of the nanocellulose dispersion produced according to Example 1 (0.08% by weight, 2 min. ultrasound). A D50 value of 281 nm and also a D90 value of 330 nm are obtained.

The invention claimed is:

1. Process for producing a dispersion containing particles of amorphous cellulose comprising
   a) providing amorphous cellulose having a less than 20% by weight fraction of crystalline regions, wherein the amorphous cellulose used has an average degree of polymerization $DP_{cuoxam}$ in the range from 350 to 1500,
   b) optionally partially hydrolyzing said amorphous cellulose; and
   c) subsequently taking up said cellulose in water or a water-containing liquid medium and simultaneously or subsequently dispersing said cellulose by input of energy, wherein the energy input in step c) is at least 2000 kWh/t with regard to the mass of the amorphous cellulose provided, and optionally, finally diluting said dispersed cellulose with water, wherein no dispersant is added before, during or after the dispersing step c); and wherein the volume-average particle size (D50 value) of the particles is less than 200 nm, determined by dynamic laser light scattering.

2. Process according to claim 1, wherein the D90 value of the dispersed particles is less than 200 nm.

3. Process according to claim 1, wherein the amorphous cellulose is obtained from chemical pulp, paper-grade pulp, microcrystalline cellulose or linters cellulose.

4. Process according to claim 1, wherein a hydrolysis in step b) is effected by means of a mineral acid or salt hydrate melt.

5. Process according to claim 1, wherein after hydrolysis the reaction mixture is freed of salts dissolved therein and the residual salt content of the hydrolysis product is less than 5% by weight.

6. Process according to claim 1, wherein the input of energy in step c) is effected via ultrasonicators, high-speed stirrers, dispersing devices based on the rotor-stator principle, jet dispersers or high shear dispersing devices.

7. Process according to claim 1, wherein the input of energy in step c) is effected in at least two stages comprising the input of energy in a first stage via a dispersing device based on the rotor-stator principle followed by the input of energy in a second stage via a high shear dispersing device.

8. Process according to claim 1, wherein the dispersion obtained in step c) has a solids concentration of the cellulose in the range from 0.1% to 10% by weight.

9. Process according to claim 1, wherein step c) is carried out at temperatures of 10 to 100° C.

10. Process according to claim 1, wherein the amorphous cellulose provided by step (a) is made by dissolving a starting cellulose in a solvent that is N methylmorpholine N oxide monohydrate, a salt hydrate melt, or an ionic liquid, and subsequently is reprecipitated by addition of a non solvent that is alcohol, water or mixtures thereof.

11. The process according to claim 1 wherein the water or water-containing medium for dispersing the particles in Step (c) has a pH above 5.

* * * * *